US00PP21873P2

(12) United States Plant Patent
Jury

(10) Patent No.: US PP21,873 P2
(45) Date of Patent: Apr. 19, 2011

(54) ***MICHELIA* PLANT NAMED 'MICJUR01'**

(50) Latin Name: ***Michelia yunnanensis*×hybrid**
Varietal Denomination: MICjur01

(76) Inventor: Mark Jury, Waitara (NZ)

( * ) Notice: Subject to any disclaimer, the term of this patent is extended or adjusted under 35 U.S.C. 154(b) by 0 days.

(21) Appl. No.: 12/460,359

(22) Filed: Jul. 18, 2009

(51) Int. Cl.
*A01H 5/00* (2006.01)

(52) U.S. Cl. ..... Plt./223

(58) Field of Classification Search ..... Plt./223
See application file for complete search history.

*Primary Examiner* — Kent L Bell

(57) ABSTRACT

A new and distinct *Michelia* cultivar named 'MICJUR01' is disclosed, characterized by having an robust, compact growth habit and large light pink flowers. The new variety is a *Michelia*, normally produced as a small ornamental tree.

2 Drawing Sheets

Latin name of the genus and species: *Michelia yunnanensis*×hybrid.

Variety denomination: 'MICjur01'.

BACKGROUND OF THE INVENTION

The new cultivar is a product of a planned breeding program. The new variety resulted from a crossing performed in 1996 in North Taranaki, Nth Is, New Zealand. The seed parent is the unpatented, unnamed *Michelia yunnanensis*. The pollen parent is the unpatented variety *Michelia* hybrid 'Mixed Up Miss'. The new variety was selected 2001, by the inventor, Mark Jury at a commercial nursery in North Taranaki, Nth Is, New Zealand.

Asexual reproduction of the new cultivar 'MICjur01' by vegetative cuttings was first in performed in 2002 at a commercial nursery in New Zealand and has shown that the unique features of this cultivar are stable and reproduced true to type on successive generations.

SUMMARY OF THE INVENTION

The cultivar 'MICjur01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MICjur01' These characteristics in combination distinguish 'MICjur01' as a new and distinct *Michelia* cultivar:

1. Distinctively large flower.
2. Robust growth.
3. Compact growth habit.
4. Light pink flowers.

PARENT COMPARISON

Plants of the new cultivar 'MICjur01' are similar to plants of the seed parent, *Michelia yunnanensis* in most horticultural characteristics, however, plants of the new cultivar 'MICjur01' have larger flowers with light pink coloration, rather than the all white flowers of the parent variety.

Plants of the new cultivar 'MICjur01' are similar to plants of the pollen parent, *Michelia* hybrid. 'Mixed up Miss' in most horticultural characteristics, however, plants of the new cultivar 'MICjur01' have larger flowers with more pink coloration, then the pollen parent. Additionally, the new variety produces more flowers, which open more slowly than those of the pollen parent.

BRIEF DESCRIPTION OF THE PHOTOGRAPH

Figure 1:
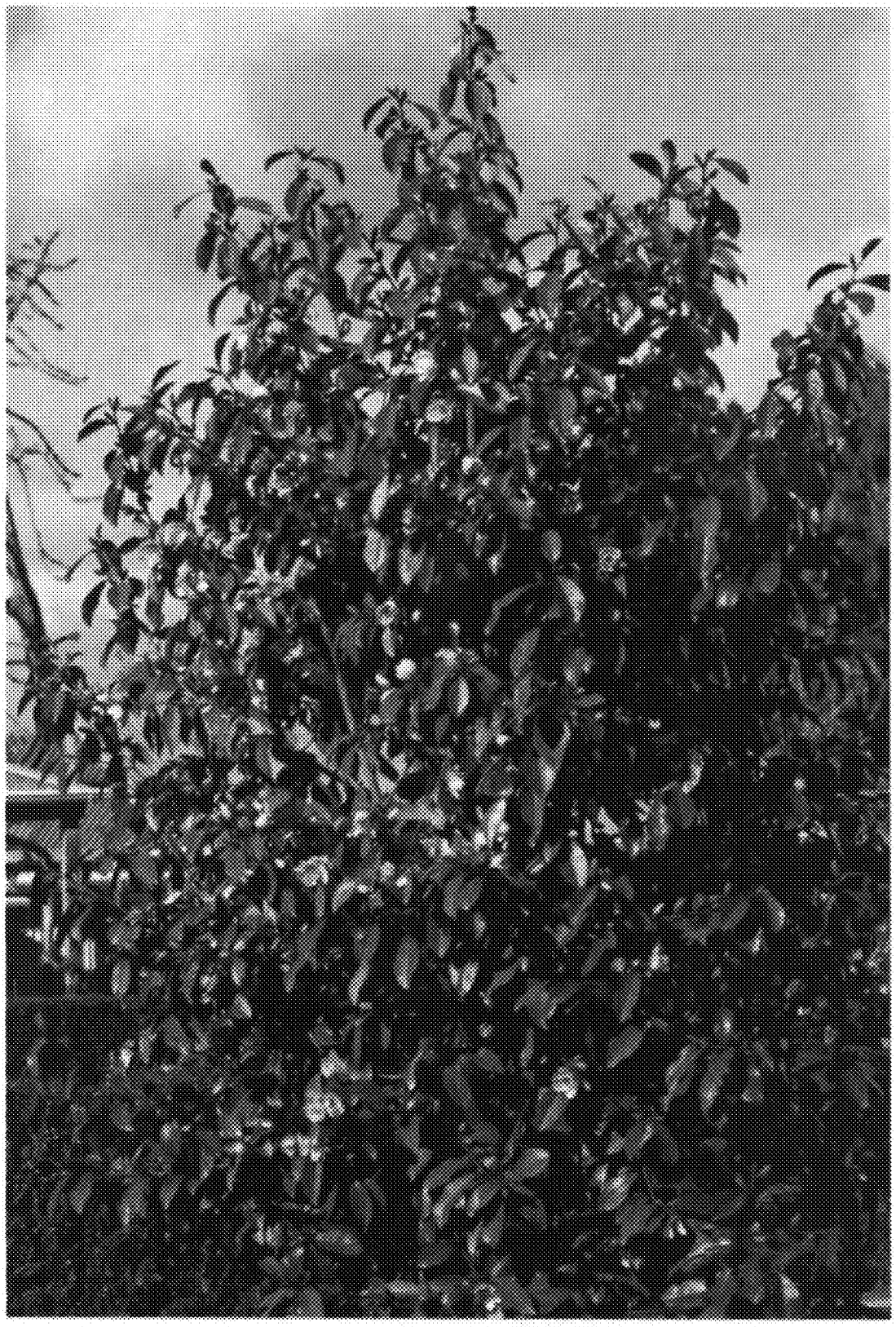

The accompanying photograph in FIG. 1 illustrates in full color a typical plant of 'MICjur01' outdoors. Age of the plant photographed is approximately 6 years from a rooted cutting.

Figure 2:
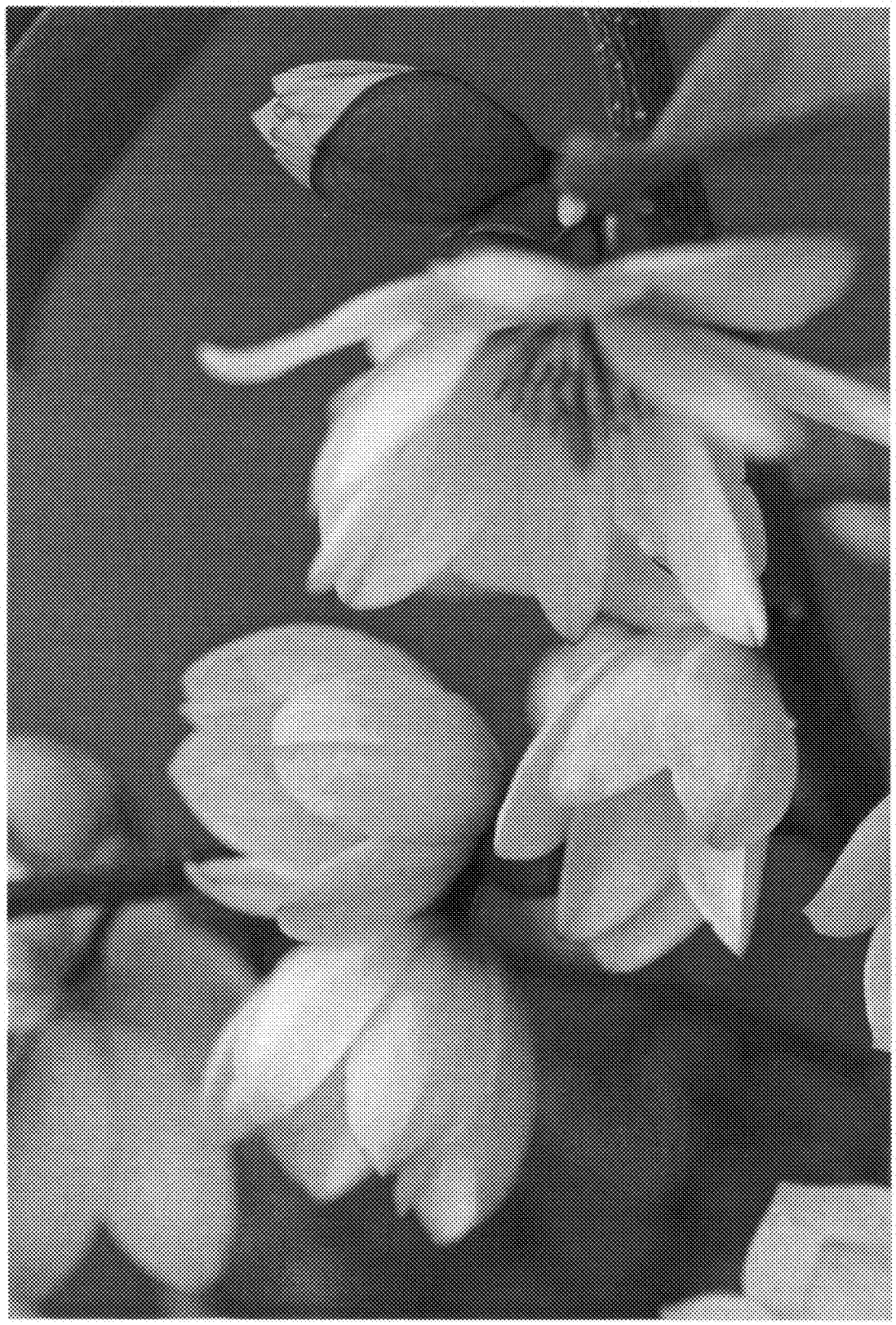

FIG. 2 illustrates in full color typical flowers of 'MICjur01'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'MICjur01' plants grown outdoors in New Zealand. Growing conditions are similar to USDA Zone 7. Age of the plants when described is approximately 4.5 years old. Measurements and numerical values represent averages of typical plant types.

Botanical classification: *Michelia yunnanensis*×hybrid 'MICjur01'.

PROPAGATION

Time to initiate roots: About 60 days at approximately 21° C.

Time to produce a rooted cutting: About 120 days at 21° C.

Root description: Typical *Michelia* root, thick, coarse, colored near RHS White 155A.

PLANT

Growth habit: Upright, spreading small evergreen tree.

In a container or in the ground: Ground.

Height: Approximately 4 meters.

Plant spread: Approximately 3 meters.
Growth rate: Approximately 10 years to reach 4 meters.
Branching characteristics: Normally a single trunk tree with lateral branches forming at acute angles, 15-30 degree, to the trunk.
*Individual branch characteristics* (*of* 4.5 *year old tree*).—Length: up to 50 cm. Diameter: up to 2 cm. Texture: slightly foveolate. Color: Near RHS Brown 200A and 200B, both colors present individually.
Trunk:
*Diameter.*—Approximately 15 cm, after 8 years. Measured approximately 10 cm above the ground.
*Texture.*—Slightly foveolate.
*Color.*—Near RHS Brown 200B.

FOLIAGE

Leaf:
*Arrangement.*—Mixed alternate, and occasionally opposite.
*Average length.*—Approximately 13 cm.
*Average width.*—Approximately 5.5 cm.
*Shape of blade.*—Ovate.
*Apex.*—Acute.
*Base.*—Rounded.
*Margin.*—Entire.
*Texture of top surface.*—Smooth, leathery.
*Texture of lower surface.*—Smooth.
*Leaf internode length.*—Approximately 3 cm.
*Color.*—Young foliage upper side: Near RHS Green 138A. Young foliage under side: Near RHS Green 138A.
*Diameter.*—0.5 cm.
*Color.*—Near RHS Greyed-Purple 183B.
Petals:
*Petal arrangement.*—Whorled, overlapping.
*Shape.*—Elliptic.
*Size.*—Length: 4.0 cm. Width: 2.3 cm.
*Margin.*—Entire.
*Apex.*—Acute.
*Base.*—Rounded.
*Petal quantity.*—Approximately 9 to 13.
*Texture.*—Smooth.
Color: Petals: When opening: Upper surface: Near RHS Red-Purple 63C. Lower surface: Near RHS Red-Purple 63B. Fully opened: Upper surface: Near RHS Red-Purple 62D, margin near RHS Red-Purple 63C. Lower surface: Near RHS Red-Purple 62D, margin near RHS Red-Purple 63C. Color Changes when aging: Maintains the same tone, becomes slightly lighter, background becomes more White N155C.
Bud:
*Shape.*—Ovate.
*Length.*—Approximately 2 cm.
*Diameter.*—Approximately 1 cm.
*Color.*—Near RHS Red-Purple 63C, margin near RHS Red-Purple 63B. Mature foliage upper side: Near RHS Green 138A. Mature foliage under side: Near RHS Green 138A.
*Venation.*—Type: Pinnate. Venation color upper side: Near RHS Yellow-Green 144A. Venation color under side: Near RHS Green 143C.
*Petiole.*—Not present, sessile.

FLOWER

Natural flowering season: Flowering begins mid Spring. Lasts approximately 10 weeks.
Begins flowering after how many years/months: 1.5 to 2 years after planting an unrooted cutting.
Inflorescence type and habit: Singly occurring star shaped, profuse flowering.
Rate of flower opening: Approximately 6 days from bud to fully opened flower.
Flower longevity on plant: 4 to 5 days, after fully opened.
Quantity of flowers: Profuse, thousands per tree.
Inflorescence size:
*Diameter.*—Approximately 6 cm.
*Length.*—Approximately 4 cm.
Pedicel:
*Length.*—0.5 cm.
Sepals/tepals: Not Present.
Fragrance: Slight.

REPRODUCTIVE ORGANS

Stamens:
*Number.*—Approximately 25.
*Filament length.*—Approximately 1.5 cm.
*Filament color.*—Near RHS Greyed-Orange 163B.
Anthers:
*Length.*—Appoximately 0.2 cm.
*Shape.*—Linear.
*Color.*—Near RHS Greyed-Red 181A.
Pistil:
*Number.*—1.
*Length.*—Approximately 2 cm.
*Style.*—Length: Approximately 1.8 cm. Color: Near RHS Yellow-Green 144B.
*Pollen.*—Quantity: Moderate. Color: Near RHS Greyed-Orange 163B.

OTHER CHARACTERISTICS

Seeds and fruits: The new cultivar does not set seed. Small, dry fruit produced, not reaching maturity and dropping after approximately 10 days.
*Fruit color.*—Begins near RHS Yellow-Green 144C, changes to Brown 200B before dropping.
*Size.*—Approximately 0.7 cm long, 0.2 cm wide.
Disease/pest resistance: Neither resistance nor susceptibility to pathogens and pests common to *Michelia* have been observed.
Temperature tolerance: The new variety is suitable for growing in USDA zones 3 through 8.
What is claimed is:
1. A new and distinct cultivar of *Michelia* plant named 'MICjur01' as herein illustrated and described.

* * * * *